United States Patent [19]

Spector

[11] Patent Number: 4,629,604

[45] Date of Patent: * Dec. 16, 1986

[54] MULTI-AROMA CARTRIDGE PLAYER

[76] Inventor: Donald Spector, 380 Mountain Rd., Union City, N.J. 07087

[*] Notice: The portion of the term of this patent subsequent to Aug. 24, 1999 has been disclaimed.

[21] Appl. No.: 557,250

[22] Filed: Dec. 2, 1983

Related U.S. Application Data

[63] Continuation-in-part of Ser. No. 477,353, Mar. 21, 1983, which is a continuation-in-part of Ser. No. 412,080, Aug. 27, 1982.

[51] Int. Cl.$^4$ .......................... A61L 9/03; G03B 21/50
[52] U.S. Cl. ...................................... 422/124; 352/85; 352/92; 422/5; 422/125
[58] Field of Search .................. 422/4, 5, 123, 125, 422/119, 124; 239/43, 53-57; 352/20, 23, 85, 92

[56] References Cited

U.S. PATENT DOCUMENTS

| | | | |
|---|---|---|---|
| 2,144,190 | 1/1939 | Merz | 352/85 X |
| 2,540,144 | 2/1951 | Stern | 352/85 X |
| 2,562,959 | 8/1951 | Stern | 352/85 |
| 2,562,960 | 8/1951 | Stern | 352/85 |
| 2,905,049 | 9/1959 | Laube | 422/4 X |
| 2,931,880 | 4/1960 | Yaffe | 422/4 X |
| 3,436,191 | 4/1969 | McGoff et al. | 422/119 X |
| 3,711,023 | 1/1973 | Smith | 239/55 X |
| 3,795,438 | 3/1974 | Westenholz et al. | 352/85 |
| 3,895,928 | 7/1975 | Moran | 422/119 |
| 3,908,905 | 9/1975 | Von Phillip et al. | 239/55 X |
| 4,306,892 | 12/1981 | Atalla et al. | 422/4 X |
| 4,346,059 | 8/1982 | Spector | 422/125 |
| 4,385,814 | 5/1983 | Elliot | 352/20 X |

Primary Examiner—Barry S. Richman
Assistant Examiner—B. P. Heaney
Attorney, Agent, or Firm—Michael Ebert

[57] ABSTRACT

A player for a multi-aroma cartridge constituted by a planar array of like frame assemblies held within a multi-section framework, each assembly being formed by a pad of absorbent material sandwiched between a pair of frames whose margins are joined together to define a central zone exposing the pad. The pad of each assembly is impregnated with a liquid fragrance that differs from those of the others. When the cartridge is inserted in a slot in the player case, it lies over a complementary honeycomb, each of whose cells is then in registration with a respective assembly. The cells are provided with individual electric heaters such that when a selected cell heater is energized, it heats the air in the cell to produce a positive pressure therein that acts to force the heated air through the zone to volatilize the liquid fragrance, the resultant aromatic vapor being discharged into the atmosphere through vents in the case. The selection of aromas to be played may be effected manually or it may be synchronized to follow the scenes of a video tape or movie film presentation.

9 Claims, 10 Drawing Figures

U.S. Patent   Dec. 16, 1986   Sheet 1 of 3   4,629,604
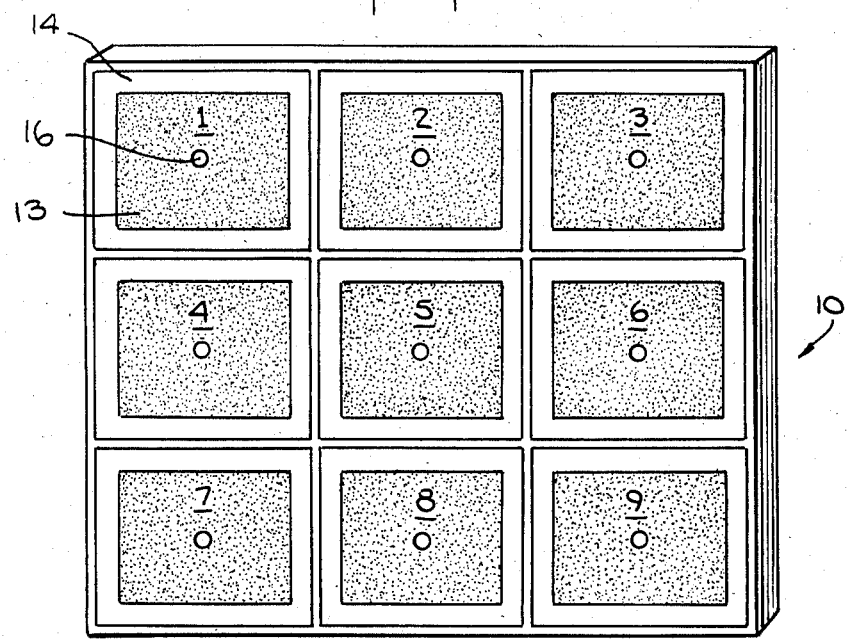
Fig. 1.
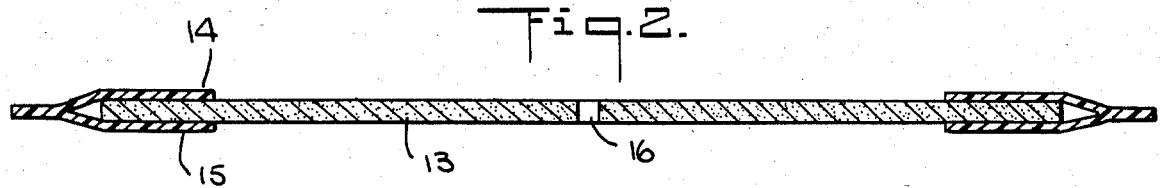
Fig. 2.
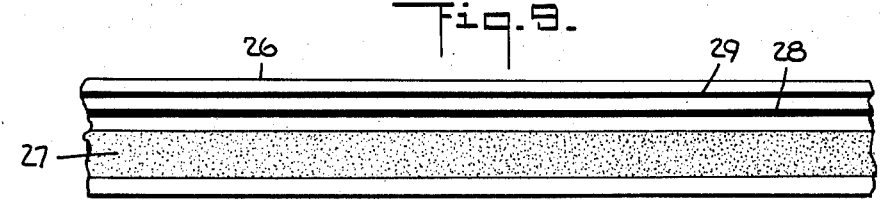
Fig. 3.
Fig. 9.

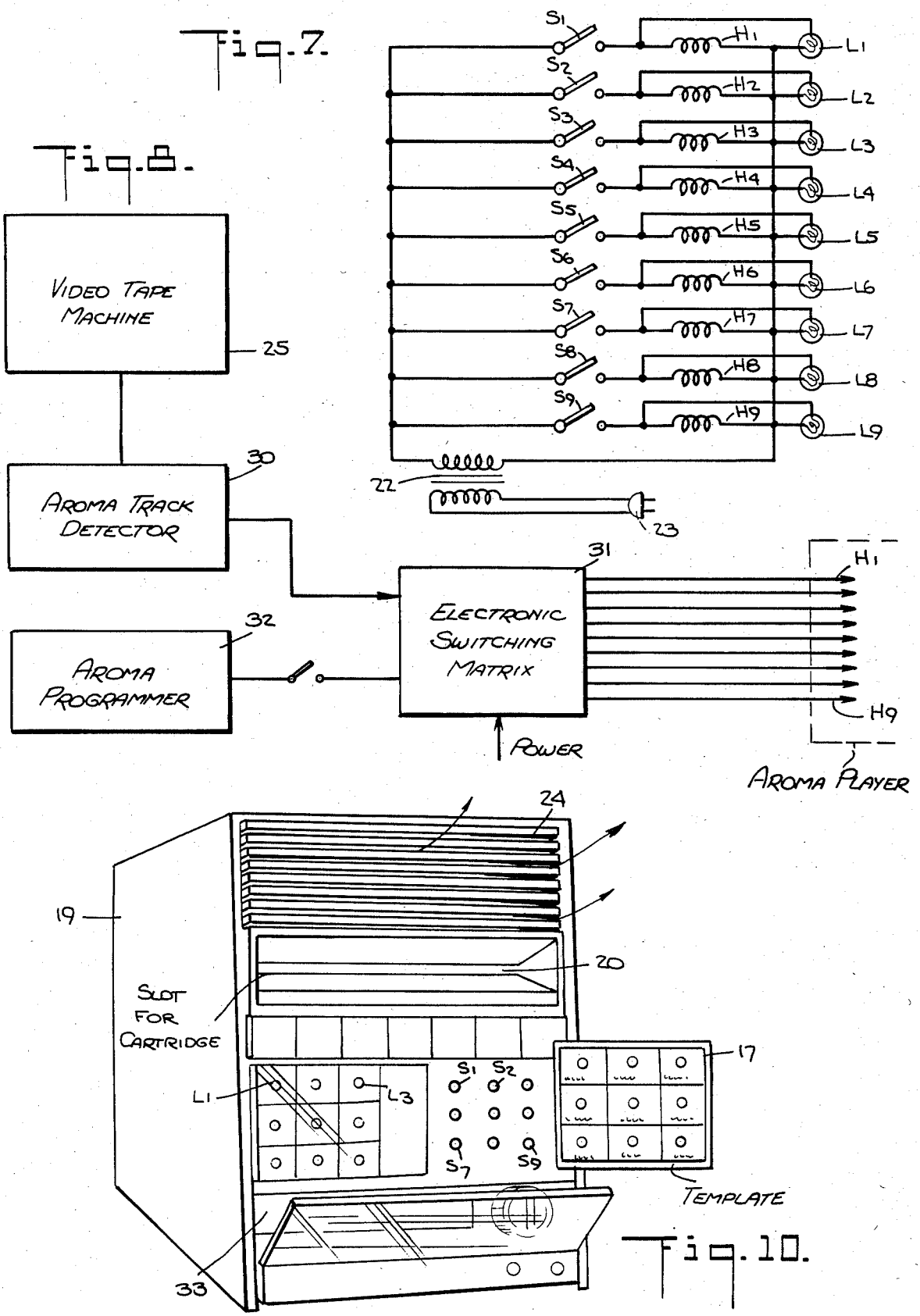

MULTI-AROMA CARTRIDGE PLAYER

RELATED APPLICATIONS

The present application is a continuation-in-part of my copending application Ser. No. 477,353, filed Mar. 21, 1983 entitled "Disc-Playing Aroma Generator", which in turn is a continuation-in-part of my application Ser. No. 412,080, filed Aug. 27, 1982 entitled "Aroma Generating Unit". The entire disclosures of these related cases are incorporated herein by reference.

BACKGROUND OF INVENTION

Field of Invention

This invention relates generally to an aroma cartridge player, each cartridge of which holds a planar array of frame assemblies capable of selectively exuding different aromatic fragrances, and in particular to a player of this type in which the selection of aromas may be effected manually or caused to follow the scenes of a video or film presentation.

As used herein, the term "aroma" is not limited to pleasant or savory smells, but encompasses scents, some of which may be unpleasant, that act to condition, modify, or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with alcohol.

The relationship of aromas to emotions and moods is well established. Thus, the antiseptic aroma which typically pervades a hospital is known to have a depressing effect on both patients and visitors, while the smell of a skunk is repellent to animals and human beings. On the other hand, an aggreeable odor, such as that produced by a sea breeze or by certain foods as they are being cooked, are pleasantly stimulating.

In order to exploit this interaction between aromas and human responses, attempts have heretofore been made to create a movie, called a "smellie" in which aromas are synchronized with the action. Thus in a romantic scene, the aroma then generated in the theatre could be a seductive feminine fragrance; whereas in a movie scene showing a wooden structure on fire, an odor suggestive of burning wood can then be exuded.

The "smellie" concept has not been successfully realized in practice, mainly because of the practical difficulty of subjecting all members of a theatre audience to a particular odor while a given scene is being played and supplanting this odor with a very different odor when shifting to a new scene.

Thus, in the example given above, should a romantic scene be relatively brief and be followed by a fire of longer duration, the first problem faced by the "Smellie" system is how, while the first scene is being played, to subject the audience to a romantic fragrance before this scene is concluded, and the second problem is how to erase this fragrance so that it does not run into the fire scene where it is clearly inappropriate.

In my prior U.S. Pat. No. 4,346,059, whose entire disclosure is incorporated herein, there is disclosed an aroma generator in which a liquid fragrance impregnates a porous pad that is placed over an opening in an otherwise enclosed housing having an electrical heater therein. When the heater is energized, it acts to heat and expand the air confined in the housing to create a pressure differential between the heated air in the housing and the atmosphere, this differential functioning to force the heated air through the pad to rapidly volatilize the liquid and exude an aromatic vapor into the atmosphere.

The present invention includes a similar aroma generator, but in conjunction with a multi-aroma cartridge capable of selectively exuding many different aromas.

SUMMARY OF INVENTION

In view of the foregoing, the main object of this invention is to provide a multi-aroma cartridge player, each cartridge of which holds an array of frame assemblies capable of exuding different aromatic fragrances.

More particularly, an object of this invention is to provide a player of the above type in which the selection of aromas may be effected manually or may be synchronized to follow the scenes of a video or film presentation.

A significant feature of the invention is that the heat mechanism by which the fragrance molecules are caused to rise in the chamber or theatre in which the player is installed acts to drive the cooler molecules of the previously-emitted fragrance to the ground, so that each newly-emitted fragrance acts effectively to wipe out the previously-emitted fragrance, making it possible to effect relatively rapid changes in fragrance in synchronism with a visual and/or musical presentation.

Also an object of this invention is to provide an aroma player which may be pre-programmed to play aromas in any desired sequence in the course of an operating cycle.

Yet another object of the invention is to provide an aroma player which operates efficiently and reliably and which may be mass-produced at relatively low cost.

Briefly stated, these objects are attained in a player for a multi-aroma cartridge constituted by a planar array of like frame assemblies held within a multi-section framework, each assembly being formed by a pad of absorbent material sandwiched between a pair of frames whose margins are joined together to define a central zone exposing the pad. The pad of each assembly is impregnated with a liquid fragrance that differs from those of the others. When the cartridge is inserted in a slot in the player case, it lies over a complementary honeycomb, each of whose cells is then in registration with a respective assembly. The cells are provided with individual electric heaters such that when a selected cell heater is energized, it heats the air in the cell to produce a positive pressure therein that acts to force the heated air through the zone to volatilize the liquid fragrance, the resultant aromatic vapor being discharged into the atmosphere through vents in the case. The selection of aromas to be played may be effected manually or it may be synchronized to follow the scenes of a video tape or movie film presentation.

OUTLINE OF DRAWINGS

For a better understanding of the invention as well as other objects and further features thereof, reference is made to the following detailed description to be read in conjunction with the accompanying drawings, wherein:

FIG. 1 is a perspective view of an aroma cartridge according to the invention;

FIG. 2 is a cross section taken through one of the frame assemblies included in the cartridge;

FIG. 3 is a template to be used with an aroma player for the cartridge;

Figure 6:
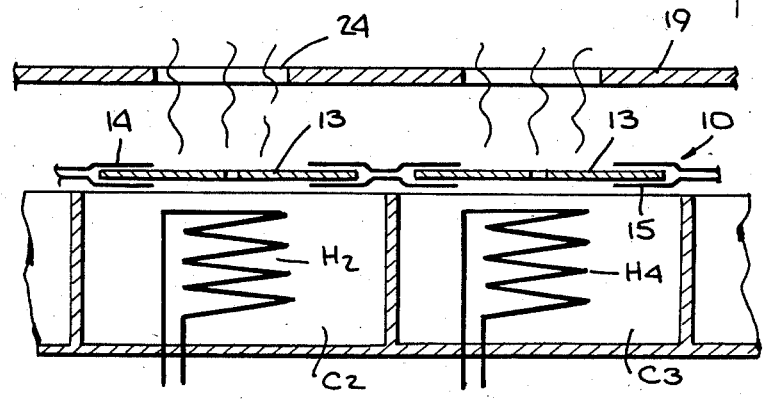

FIG. 6 schematically illustrates the operative relationship of the honeycomb to the cartridge;

FIG. 7 is the schematic circuit diagram of the aroma player;

FIG. 8 is a block diagram of a system coordinating a video tape machine with the aroma player;

FIG. 9 is a piece of the video tape which includes a sync signal track for the aroma player; and FIG. 10 shows a preferred practical embodiment of the aroma player.

DESCRIPTION OF INVENTION

Multi-Aroma Cartridge

Referring now to FIGS. 1 and 2, there is shown a multi-aroma cartridge in accordance with the invention, the cartridge including a rectangular framework 10 divided by horizontal and vertical ribs into rectangular coordinate sections for holding a rectangular array of nine frame assemblies designated by numerals 1 to 9.

While the cartridge shown is designed for nine frame assemblies, in practice a greater or a smaller number may be used. The larger the number, the greater the choice of aromas available from each cartridge. The framework 10 may be molded of synthetic plastic material.

Each frame assembly, as shown in FIG. 2, is composed of a pad 13 of porous material having good wicking properties, such as blotting paper, non-woven fabric or foam plastic material, sandwiched between a pair of frames 14 and 15. The margins of the frames are sealed together to define a central zone Z which exposes the pad on both sides thereof. In practice, a small hole 16 may be bored in the center of the pad to relieve excessive air pressure.

Frames 14 and 15 may be of synthetic plastic material such as PVC or other plastic which may be marginally sealed ultrasonically or by heat-pressure to create an envelope for holding the pad. Each pad is impregnated with a distinctive liquid fragrance after the cartridge is assembled, the liquid being dispersed throughout the entire pad because of its wicking properties. Because there are nine frame assemblies, the cartridge holds nine different fragrances.

In practice, the nine assemblies may be fabricated using a single pad of foam plastic material sandwiched between a pair of plastic sheets having rectangular cutouts to define the individual frames, the sheets and the pad then being interbonded by ultrasonic or other sealing means along vertical and horizontal lines to create the individual frame assemblies.

Associated with each cartridge is an identifying template 17, as shown in FIG. 7, which has the same dimensions as the cartridge and is divided by printed lines into nine coordinate sections 1 to 9, each section having a center bore 18 to accommodate a switch button which when pressed will activate the frame assembly having the same number.

Each numbered section on the template identifies the fragrance of the correspondingly numbered section of the cartridge. Thus number 1 on the template is "Ocean Breeze," number 2 is "Lime," number 3 is "Rain," etc., so that when the activating button for section 8 on the player is pressed, the player then emits a "Rose" scent.

The Aroma Player

Figure 4:
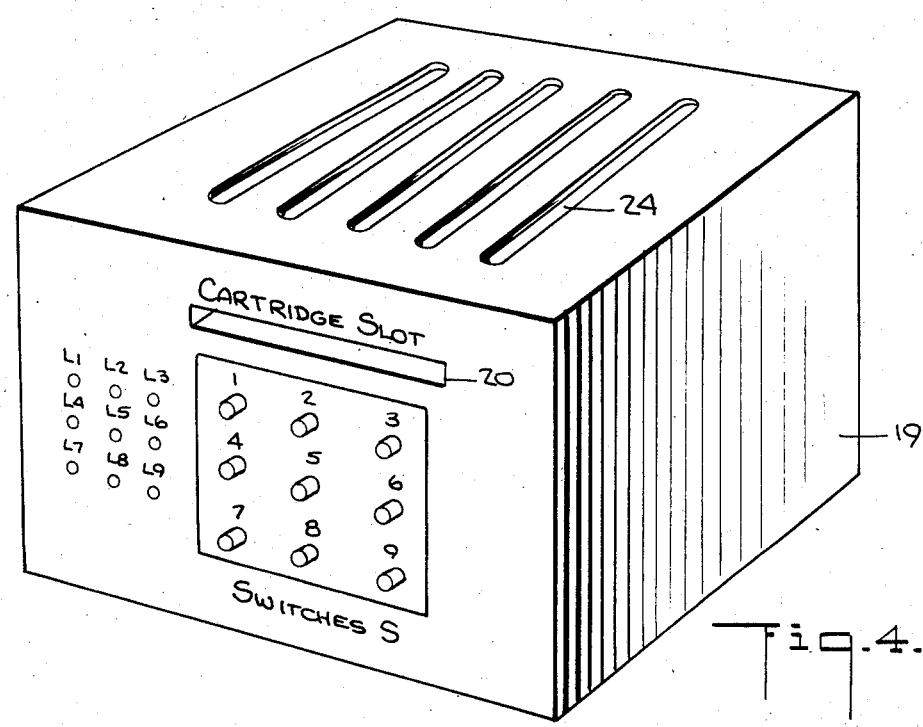
FIG. 4 illustrates the aroma player.
Figure 5:
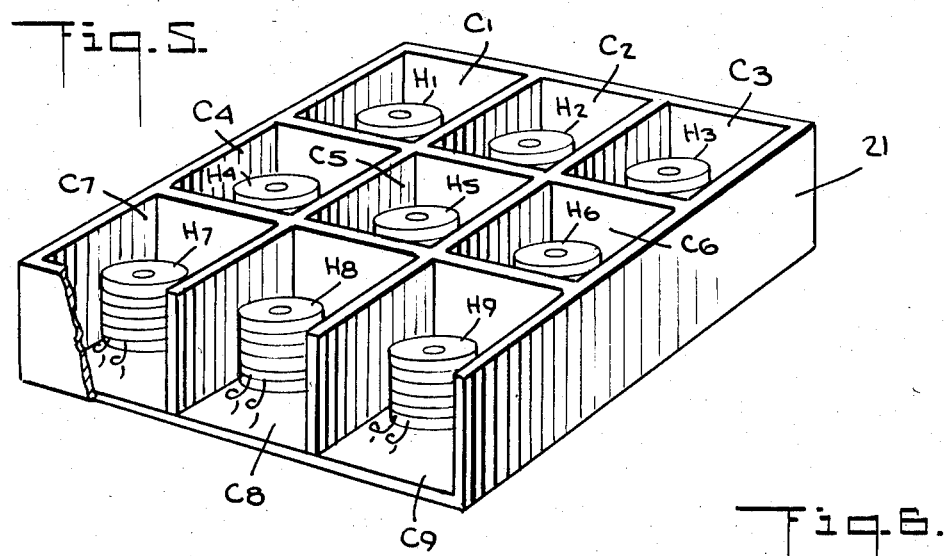
FIG. 5 shows the cellular honeycomb included in the player.

As shown in FIG. 4, an aroma player in accordance with the invention includes a box-like case 19 having a slot 20 on its front panel to receive a cartridge 10 which when inserted therein overlies a honeycomb 21. This honeycomb is shown separately in FIG. 5.

Honeycomb 21 is composed of nine open-top, box-like cells $H_1$ to $H_9$ which complement sections 1 to 9 on the cartridge so that when the cartridge overlies the honeycomb, the cartridge assemblies 1 to 9 then lie in registration with the correspondingly numbered cells $H_1$ to $H_9$, thereby covering and enclosing each cell.

An individual electric heater is mounted on the base of each cell; hence in the honeycomb, we find cell heaters $H_1$ to $H_9$. The circuit arrangement for these heaters is shown in FIG. 7, where it will be seen that each heater ($H_1$ to $H_9$) and an associated pilot light bulb ($L_1$ to $L_9$) is connected through a respective switch ($S_1$ to $S_9$) to the secondary winding of a stepdown transformer 22 whose primary winding is connected by way of a plug 23 to a standard 120 V power line. The heaters and bulbs are all of the 6, 12 or 24 volt type so that the player operates safely at relatively low voltage.

When any one of the switches $S_1$ to $S_9$ is closed, the associated heater is energized, such as heater $H_2$ in cell $C_2$ shown in FIG. 6. As a consequence, the air confined within this closed cell $C_2$ is caused to rise in temperature and expand to create a positive pressure in the cell. Because of the resultant pressure differential between the heated air in the cell and the external atmosphere, the hot air is forced through the liquid-impregnated pad 13 in the exposure zone Z, and the liquid is volatilized to produce an aromatic vapor. This vapor is discharged through vents 24 in the case of the player.

The cells whose heaters are not energized remain passive, and the only odor which is emitted by the player is that associated with an energized cell. When one switch is turned off and another is then turned on, the vapor molecules from the inactivated cell proceed to cool, whereas the newly activated cell yields heated vapor molecules which drive the cool molecules to the ground and thereby effectively wipe out the previously emitted odor.

This action, in which one fragrance supplants the previously-generated fragrance, does not take place immediately, but the action is fast enough to permit a series of emissions without interference therebetween within, say, a one-hour period.

Thus if one first plays "Lime" (2) for 10 minutes and then switches over to, say, "Orchid" (6), within about a minute, the lime odor fades out, to be supplanted by orchid. And when one wishes to play with an altogether new set of odors, the multi-aroma cartridge can then be withdrawn from the player and replaced with a cartridge holding the new set.

Entertainment System

In the arrangement shown in FIG. 8, the operation of the aroma player 10 is coordinated with a video tape machine 25 which operates in conjunction with a TV terminal to present a movie or other form of entertainment in a manner whereby the operation of the aroma player is synchronized with the scenes being presented.

To this end, magnetic tape 26 of the video machine includes not only, as shown in FIG. 9, the usual video track 27 and sound track 28, but also a sync signal track 29 which at the beginning of each scene carries a switch-on digital signal identifying a particular cell heater by a suitable binary code number, and at the conclusion that scene carries a switch-off binary code signal for that heater and no other.

The sync signal track 29 is associated with a suitable magnetic detector head 30 which picks up the sync signals from the tape and applies them to an electronic switching matrix 31. The matrix acts to decode the signals to selectively switch power on and off in the appropriate heaters ($H_1$ to $H_9$).

These recorded sync signals function to activate that frame assembly in the cartridge being played which generates a fragrance appropriate to the scene being presented on the screen. If, therefore, a given scene is one showing actors walking through rain, the sound track will concurrently supply the sound of rain, while the smell of rain is, at the same time, generated by the "Rain" assembly of the cartridge.

The human sensory system is highly sensitive to odors; and an entertainment system which accompanies each scene with scents as well as sounds appropriate thereto is far more effective in evoking an emotional response from the audience than one which subjects the audience to an unchanging olfactory environment.

Obviously, the choice of fragrances on a particular cartridge will be related to the nature of the entertainment being presented by the video recording, and not every scene will necessarily be accompanied by a distinctive odor if only nine assemblies are available on the cartridge. However, it will be appreciated that a choice of nine different odors per cartridge affords a reasonably good range of mood changes.

The invention is not limited to video tape or movie film which can be modified to include a fragrance sync signal track; for a track of this type can also be used with disc recordings. Also, a separate sync track is not essential; for the fragrance sync signals can be impressed as supersonic signals superimposed on the sound track and separated therefrom by a filter which rejects the relatively low-frequency sound signals.

Alternatively, where one wishes in the course of an hour or some other predetermined period to modulate environmental fragrances without a visual presentation, a programmer 32 could be used in conjunction with the electronic switching matrix. This programmer may take the form of a microprocessor operating in conjunction with a clock to feed into the decoding matrix at timed intervals during a given operating cycle, a sequence of code numbers sequentially activating the desired aroma assemblies. These code numbers can be entered into the microprocessor by a keyboard and changed at the discretion of the user.

Rather than the use of a single frame assembly for each distinctive odor, the cartridge may contain fragrances which are blendable to create new fragrances in a manner analogous to the additive mixing of primary colors to produce a full spectrum of different colors. In that case, one activates simultaneously more than one cell heater.

Preferred Embodiment

In the instrument shown in FIG. 10, an aroma player is integrated with a video tape machine so that one can provide visual and sound entertainment in conjunction with a synchronized aroma presentation. This instrument includes a front panel slot 20 to receive a mult-aroma cartridge 10 and a second slot 33 to receive the video tape cartridge having a sync signal track to coordinate the visually presented action with selected aromas.

Also on the front panel is a bank of switches $S_1$ to $S_9$ which cooperate with the template 17 identifying the different fragrances, and a bank of light bulbs $L_1$ to $L_9$ which identifies the fragrances being played.

While there has been shown and described a preferred embodiment of a multi-aroma cartridge player in accordance with the invention, it will be appreciated that many changes and modifications may be made therein without, however, departing from the essential spirit thereof.

Thus to ensure the emission of all vapors from the player without regard to the particular fragrance being generated, a blower may be installed in the open space between vents 24 in the case and cartridge 10 therebelow to prevent vapor from lingering in the player.

Also, since some aromas are more pungent than others, in practice one can apply more heat to some assemblies than to others. Thus to render a delicate aroma more effective, a greater amount of heat is required for the assembly which emits this aroma than is required for an assembly producing a more penetrating aroma. To this end, a variable resistor may be placed in series with each of the switches ($S_1$ to $S_9$ in FIG. 7), so that each heater can be separately adjusted to provide a level of heat appropriate to the corresponding fragrance assembly.

And when the heaters are actuated, as in the arrangement shown in FIG. 8, by sync signals derived from a video tape track, the track may also have recorded thereon sync-related heater level signals which when decoded instruct a computerized control system to electronically adjust the ohmic value of resistance to be inserted in the circuit of the sync-activated heater to afford the proper level of heat.

I claim:
1. An aroma generator kit comprising:
 (A) a replaceable cartridge having a planar array of like frame assemblies held within a multi-section framework, each assembly being formed by a pad of absorbent air-pervious material held at its peripheral edge between two frames of said multi-section framework, said two frames of each said assembly defining an open central zone exposing a central area of said pad, said central area being impregnated with a liquid fragrance wherein each said assembly carries a different liquid fragrance;
 (B) a case having a top wall, side walls, an open top multi-cell honeycomb structure contained within said case, a slot in one of said side walls for receiving said cartridge and for positioning said cartridge within said case above said honeycomb structure, each cell of said honeycomb structure being provided with a selectively activated heater, and vent means within one of said case walls at a position above said slot whereby when said cartridge is received in said slot the open top of each of said cells is in registration with a respective assembly of said cartridge and a confined air region is formed within each cell below its respective assembly; and (C) switching means associated with said case for selectively activating each of said heaters, whereby when a heater of an individual cell is activated the confined air region within said individual cell is heated resulting in a positive air pressure within said individual cell which forces air through the central area of the respective assembly thereby volatilizing the liquid fragrance of the respective assembly to produce an aromatic vapor which is discharged through said vent means.

2. A kit as set forth in claim 1, wherein said switching means associated with said case includes a bank of switches on one of said side walls of said case, each switch of said bank acting, when actuated, to activate a respective heater.

3. A kit as set forth in claim 2, wherein said one of said side walls provided with said bank of switches is further provided with a corresponding bank of indicator lights, each indicator light acting, when a respective switch is actuated, to indicate which respective heater has been activated.

4. A kit as set forth in claim 2, wherein the switches in said bank of switches are push-button switches, said switches are deployed in an array corresponding to the planar array of said cartridge.

5. A kit as set forth in claim 4, further comprising a template positioned on said bank of switches, said template having dimensions corresponding to said bank of switches and said template being divided into sections arranged in an array corresponding to said planar array of said cartridge, each section of said template having a hole therein which registers with a corresponding push-button switch in said bank of switches, and each section of said template including means identifying the fragrance of the corresponding assembly of said cartridge.

6. A kit as set forth in claim 1 in combination with an apparatus for producing a visual presentation on a screen, said apparatus comprising means for displaying a series of different scenes on a screen and means for synchronizing the operation of the switching means of the kit with the operation of said apparatus, said switching means including a switching matrix for selectively actuating each of said heaters, whereby the display of each scene of said series actuates said synchronizing means which in turn activates said switching matrix which in turn selectively actuates a particular heater of said kit thereby discharging a particular aroma to accompany each scene of said series.

7. The combination as set forth in claim 6, wherein said apparatus comprises a video tape recorder and player, said series of scenes being recorded on a video track of a video tape, and said synchronizing means including a track of sync signals on said video tape in association with said video track.

8. The combination as set forth in claim 7, wherein said synchronizing means further includes a detector for detecting said sync signals from the sync track of said video tape and means responsive to said sync signals for actuating said switching matrix thereby selectively activating said heaters.

9. The combination as set forth in claim 8, wherein said sync signals are in binary coded form and are applied to said switching matrix which decodes said signals to selectively actuate the cell heaters.

* * * * *